US00PP32997P2

(12) United States Plant Patent
Heuger

(10) Patent No.: US PP32,997 P2
(45) Date of Patent: Apr. 20, 2021

(54) ***HELLEBORUS* PLANT NAMED 'COSEH 6600'**

(50) Latin Name: ***Helleborus* x *ballardiae* X *Helleborus* x *hybridus***
Varietal Denomination: COSEH 6600

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,637

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'COSEH 6600', characterized by its upright to slightly outwardly spreading and mounded plant habit; moderately vigorous to vigorous growth habit; dark green-colored leaves; freely flowering habit; greyed purple to greyed red-colored flowers; and good garden performance.

2 Drawing Sheets

Figure 1:
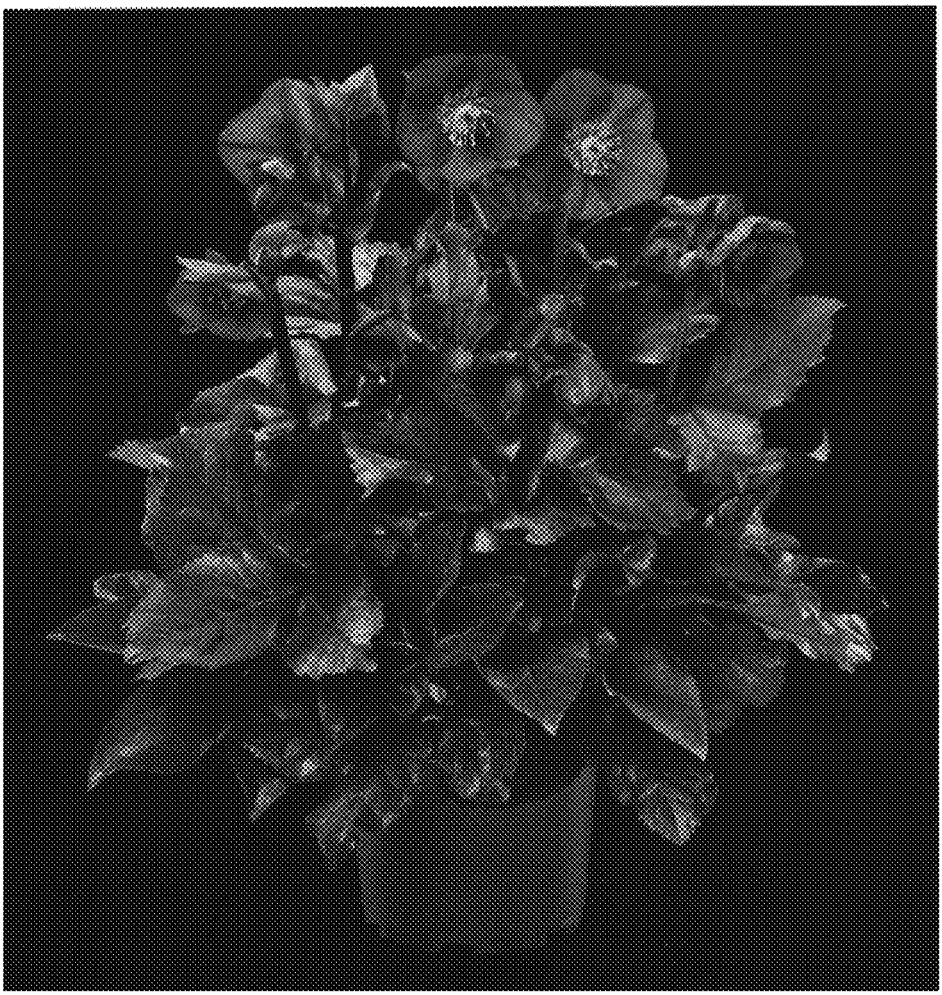

Botanical designation: *Helleborus* x *ballardiae* X *Helleborus* x *hybridus*.
Cultivar denomination: 'COSEH 6600'.

CROSS-REFERENCED TO CLOSELY-RELATED APPLICATIONS

Title: *Helleborus* Plant Named 'COSEH 6400'
Inventor/Applicant: Josef Heuger
Filed: Concurrently with the instant application Ser. No. 16/873,645
Title: *Helleborus* Plant Named 'COSEH 6500'
Inventor/Applicant: Josef Heuger
Filed: Concurrently with the instant application Ser. No. 16/873,638

STATEMENT REGARDING PRIOR DISCLOSURES BY INVENTOR/APPLICANT:

An European Community Plant Breeder's Rights application for the instant plant was filed by the Inventor/Applicant, Mr. Josef Heuger of Glandorf, Germany, on Jun. 6, 2019, application number 2019/1389. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ballardiae* X *Helleborus* x *hybridus* and hereinafter referred to by the name 'COSEH 6600'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2012 of a proprietary selection of *Helleborus* x *ballardiae* identified as code number P839, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in January, 2015.

Asexual reproduction of the new *Helleborus* plant by in vitro axillary meristem culture in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6600'. These characteristics in combination distinguish 'COSEH 6600' as a new and distinct *Helleborus* plant:

1. Upright to slightly outwardly spreading and mounded plant habit.
2. Moderately vigorous to vigorous growth habit.
3. Dark green-colored leaves.
4. Freely flowering habit.

5. Greyed purple to greyed red-colored flowers.
6. Good garden performance.

Plants of the new *Helleborus* differ from plants of the female parent selection in the following characteristics:

1. Plants of the new *Helleborus* are more vigorous than plants of the female parent selection.
2. Plants of the new *Helleborus* flower later than plants of the female parent selection.

Plants of the new *Helleborus* differ from plants of the male parent selection in the following characteristics:

1. Plants of the new *Helleborus* are more vigorous than plants of the male parent selection.
2. Flowers of plants of the new *Helleborus* are greyed purple to greyed red in color whereas flowers of plants of the male parent selection are reddish in color.

Plants of the new *Helleborus* can be compared to plants of *Helleborus* x *ballardiae* X *Helleborus* x *hybridus* 'COSEH 6400', disclosed in a U.S. Plant Patent application filed concurrently. Plants of the new *Helleborus* differ primarily from plants of 'COSEH 6400' in plant and growth habit as plants of the new *Helleborus* are shorter than and not as vigorous as plants of 'COSEH 6400'. In addition, flowers of plants of the new *Helleborus* plant are greyed purple to greyed red in color whereas flowers of plants of 'COSEH 6400' are light yellow green in color with greyed purple-colored margins.

Plants of the new *Helleborus* can be compared to plants of *Helleborus* x *ballardiae* X *Helleborus* x *hybridus* 'COSEH 6500', disclosed in a U.S. Plant Patent application filed concurrently. Plants of the new *Helleborus* differ primarily from plants of 'COSEH 6500' in flower color as flowers of plants of the new *Helleborus* are greyed purple to greyed red in color whereas flowers of plants of 'COSEH 6500' are light yellow green in color with greyed purple to greyed red-colored margins. In addition, plants of the new *Helleborus* are shorter than and not as broad as plants of 'COSEH 6500'.

Plants of the new *Helleborus* can also be compared to plants of *Helleborus* x *hybridus* 'Penny's Pink', not patented. In side-by-side comparisons, plants of the new *Helleborus* differ primarily from plants of 'Penny's Pink' in the following characteristics:

1. Plants of the new *Helleborus* have dark green-colored leaves without distinct venation whereas plants of 'Penny's Pink' have green-colored leaves with distinct venation.
2. Plants of the new *Helleborus* differ from plants of 'Penny's Pink' in flower color as plants of the new *Helleborus* have darker greyed purple-colored flowers than plants of 'Penny's Pink'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6600' grown in a container.

Figure 2:
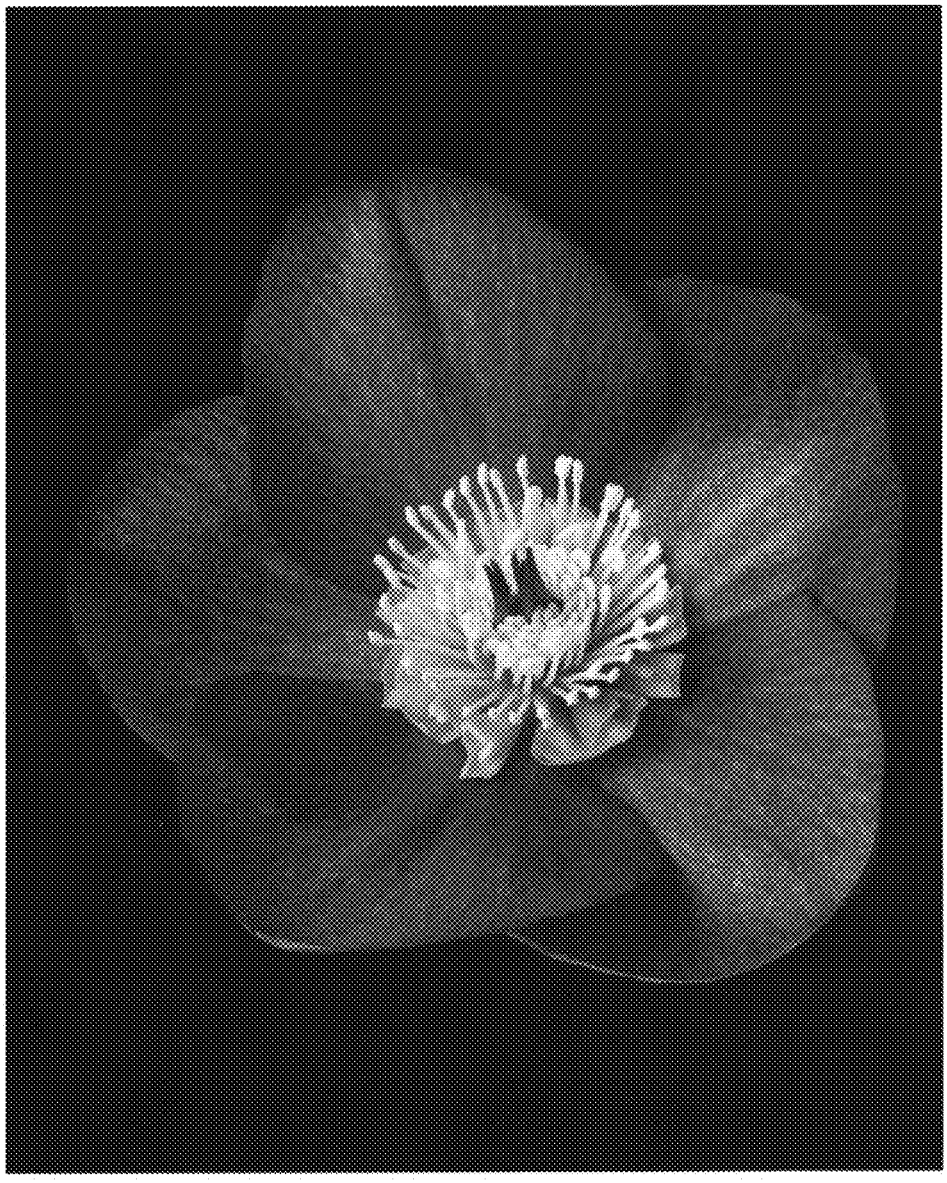

The photograph on the second sheet (FIG. 2 of 2) is a close-up view of a typical flower of 'COSEH 6600'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ballardiae* X *Helleborus* x *hybridus* 'COSEH 6600'.

Parentage:

*Female, or seed, parent*.—Proprietary selection of *Helleborus* x *ballardiae* disclosed as code number P839, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, roughly flattened globular; moderately vigorous to vigorous growth habit and moderate to rapid growth rate.

*Plant height, soil level to top of foliar plane*.—About 23 cm.

*Plant height, soil level to top of flowers*.—About 44.9 cm.

*Plant diameter* (*area of spread*).—About 66.5 cm.

Leaf description:

*Arrangement*.—Leaves arranged in a basal rosette; leaves palmately compound with typically five leaflets per leaf.

*Leaf length*.—About 18.1 cm.

*Leaf width*.—About 19.7 cm.

*Leaflet length*.—About 11.5 cm.

*Leaflet width*.—About 6.5 cm.

*Leaf shape*.—Palmate; reniform in outline.

*Leaflet shape*.—Elliptic, ovate or obovate.

*Leaflet apex*.—Acute.

*Leaflet base*.—Attenuate.

*Leaflet margin*.—Serrate; coarsely undulate.

*Leaflet texture and luster, upper surface*.—Smooth, glabrous; leathery; slightly glossy.

*Leaflet texture and luster, lower surface*.—Smooth, glabrous; leathery; matte to slightly glossy.

*Leaflet venation pattern*.—Pinnate.

*Leaflet color*.—Developing leaflets, upper surface: Close to 137A; midvein tinged at the base with close to 178A. Developing leaflets, lower surface: Close to 148A to 148B; midvein, close to 183A. Fully developed leaflets, upper surface: Darker than between NN137A and 139A; venation, close to 144C. Fully developed leaflets, lower surface: Close to between N138C and 147B; venation, close to 183A.

*Petioles*.—Length: About 14.9 cm. Diameter: About 7 mm to 8 mm. Strength: Strong. Texture and luster, upper and lower surfaces: Smooth, glabrous; slightly glossy. Color, upper and lower surfaces: Close to 144A moderately covered with fine dots, close to 197B and proximally, closer to N186C.

Flower description:

*Flower shape and habit*.—Rotate flowers; flowers moderately cupped; arranged in panicles; freely flowering habit with about seven flowers per inflorescence and about 77 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 1.5 cm. Diameter: About 1.2 cm. Shape: Broadly ovate to broadly oblong. Texture and luster: Smooth, glabrous; slightly glossy. Color: Close to 145C; venation, close to 182A.

*Inflorescence height* (*including peduncle*).—About 47.6 cm.

*Inflorescence diameter*.—About 22.7 cm.

*Flower diameter*.—About 5.8 cm by 5.8 cm.

*Flower depth* (*height*).—About 2.2 cm.

*Petals*.—All petals are transformed into nectaries.

*Sepals*.—Quantity and arrangement: About five, arranged in a single whorl. Length: About 3.5 cm. Width: About 3.3 cm. Shape: Broadly ovate, slightly concave. Apex: Obtuse. Base: Truncate to broadly cuneate. Margin: Entire; slightly undulate. Texture and luster, upper surface: Smooth, glabrous; matte. Texture and luster, lower surface: Smooth, glabrous; slightly glossy. Color: When opening, upper surface: Close to 145A; heavily flushed with 186A and 186B; venation, similar to lamina. When opening, lower surface: Close to 145C heavily flushed with close to 183B and 183C; towards the margins and apex, close to 186A; venation, close to 185B. Fully opened, upper surface: Close to 186A and 186B; center of sepal tinged with lighter than 182D; venation, similar to lamina; with development, color becoming closer to between N186C and 200B and center, moderately tinged with close to N200A to N200B. Fully opened, lower surface: Close to 186A; center of sepal tinged with close to 146D; venation, similar to lamina; with development, color becoming closer to N186C and venation, close to 187A.

*Flower bracts*.—Quantity per flower: Typically one or two. Length: About 5.3 cm. Width: About 3.4 cm. Shape: Ovate. Apex: Acute. Base: Truncate. Margin: Sparsely and finely serrate; slightly undulate. Color, upper surface: Close to NN137A; venation, similar to lamina. Color, lower surface: Close to 147B; venation, close to 200A to 200B.

*Peduncles*.—Length: About 38.9 cm. Diameter: About 8 mm. Aspect: About 20° from vertical. Strength: Strong. Texture and luster: Smooth, glabrous; moderately glossy. Color: Close to 150D, heavily covered with fine dots, close to 187B.

*Pedicels*.—Length: About 3.2 cm. Diameter: About 3 mm. Aspect: About 10° to 32.5° from peduncle axis. Strength: Moderately strong. Texture and luster: Smooth, glabrous; moderately glossy. Color: Close to 145C.

*Reproductive organs*.—Stamens: Quantity per flower: About 80. Filament length: About 1.3 cm. Filament color: Close to NN155C. Anther shape: Double and broadly reniform; basifixed. Anther size: About 2 mm by 2.25 mm. Anther color: Close to between 150C and 150D. Pollen amount: Sparse to moderate. Pollen color: Close to 4D to lighter than 4D. Pistils: Quantity per flower: About five to eight. Pistil length: About 1.1 cm. Stigma diameter: About 0.3 mm. Stigma shape: Club-shaped. Stigma color: Close to 157D. Style length: About 1 cm. Style color: Close to 186A. Ovary color: Close to 150D. Nectaries (transformed petals): Quantity per flower: About 13. Length: About 1.2 cm. Diameter: About 4 mm. Shape: Tubular, flattened. Texture and luster, inner and outer surfaces: Smooth, glabrous; slightly glossy. Color, immature, inner and outer surfaces: Close to 145C; towards the base, close to 145B. Color, mature, inner surface: Close to 145B; towards the apex, close to 145C; towards the base, close to N144B; venation, similar to lamina; with development, becoming closer to 152C and towards the apex, close to 153D. Color, mature, outer surface: Close to 145B; towards the apex, close to 145C; towards the base, close to N144B; basal spot, close to 152C; venation, similar to lamina; with development, becoming closer to 152C, towards the apex, close to 153D and basal spot, close to 152A.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6600' as illustrated and described.

* * * * *